US00PP24783P2

(12) United States Plant Patent
Ray

(10) Patent No.: US PP24,783 P2
(45) Date of Patent: Aug. 19, 2014

(54) ***HYDRANGEA* PLANT NAMED 'HAAS' HALO'**

(50) Latin Name: *Hydrangea arborescens*
Varietal Denomination: Haas' Halo

(75) Inventor: Frederick Harding Ray, Springfield, PA (US)

(73) Assignee: Plants Nouveau, LLC, Charleston, NC (US)

( * ) Notice: Subject to any disclaimer, the term of this patent is extended or adjusted under 35 U.S.C. 154(b) by 166 days.

(21) Appl. No.: 13/573,395

(22) Filed: Sep. 13, 2012

(51) Int. Cl.
*A01H 5/00* (2006.01)

(52) U.S. Cl.
USPC ..... Plt./250

(58) Field of Classification Search
CPC ..... A01H 5/02
USPC ..... Plt./250
See application file for complete search history.

*Primary Examiner* — June Hwu
(74) *Attorney, Agent, or Firm* — Penny J. Aguirre

(57) ABSTRACT

A new cultivar of *Hydrangea arborescens* named 'Haas' Halo' that is characterized by its very large lace-cap type inflorescences with 50 large sterile florets per inflorescence, its upright plant habit, its strong sturdy stems with the ability to hold up its large inflorescences and its dried flowers after blooming that are present for up to 6 months.

2 Drawing Sheets

Genus/species: *Hydrangea arborescens.*
Varietal denomination: 'Haas' Halo'.

BACKGROUND OF THE INVENTION

The present invention relates to a new and distinct cultivar of *Hydrangea arborescens* and will be referred to hereafter by its cultivar name, 'Hass' Halo'. 'Hass' Halo' represents a new cultivar of smooth *Hydrangea*, a deciduous shrub grown for landscape use.

The Inventor discovered the new *Hydrangea* as a naturally occurring whole plant mutation in summer of 2008 in a garden in Springfield, Pa. The parentage is unknown.

Asexual reproduction of the new cultivar was first accomplished by softwood stem cuttings in Earlville, Md. in may 2009 by the Inventor. Propagation has shown that the characteristics of this cultivar are stable and reproduced true to type in successive generations.

SUMMARY OF THE INVENTION

The following traits have been repeatedly observed and represent the characteristics of the new cultivar. These attributes in combination distinguish 'Haas' Halo' as a unique cultivar of *Hydrangea.*

1. 'Haas' Halo' exhibits very large lace-cap type inflorescences; about 35 cm in diameter.
2. 'Haas' Halo' exhibits an upright plant habit.
3. 'Haas' Halo' exhibits strong sturdy stems with the ability to hold up its large inflorescences.
4. 'Haas' Halo' exhibits dried flowers after blooming that are present for up to 6 months.
5. 'Haas' Halo' exhibits about 50 large sterile florets per inflorescence.

'Haas' Halo' can be most closely compared to *Hydrangea arborescens* cultivars 'Dardom' (U.S. Plant Pat. No. 14,168. and 'Annabelle' (not patented). 'Dardom' differs from 'Haas' Halo' in having inflorescences that are about half the size, in having smaller sterile florets, and in having leaves that are smaller in size and lighter in color. 'Annabelle' differs from 'Haas' Halo' in lacking lace-cap type inflorescences, in having weaker stems, in having foliage that is less leathery and lighter in color, and in having a more upright plant habit.

BRIEF DESCRIPTION OF THE DRAWINGS

The accompanying colored photograph illustrates the overall appearance and distinct characteristics of the new *Hydrangea*. The plants in the photograph is about three years in age as grown outdoors in a garden in Springfield, Pa.

The photograph in FIG. 1 provides a view of a plant of 'Haas' Halo' in bloom.

Figure 1:
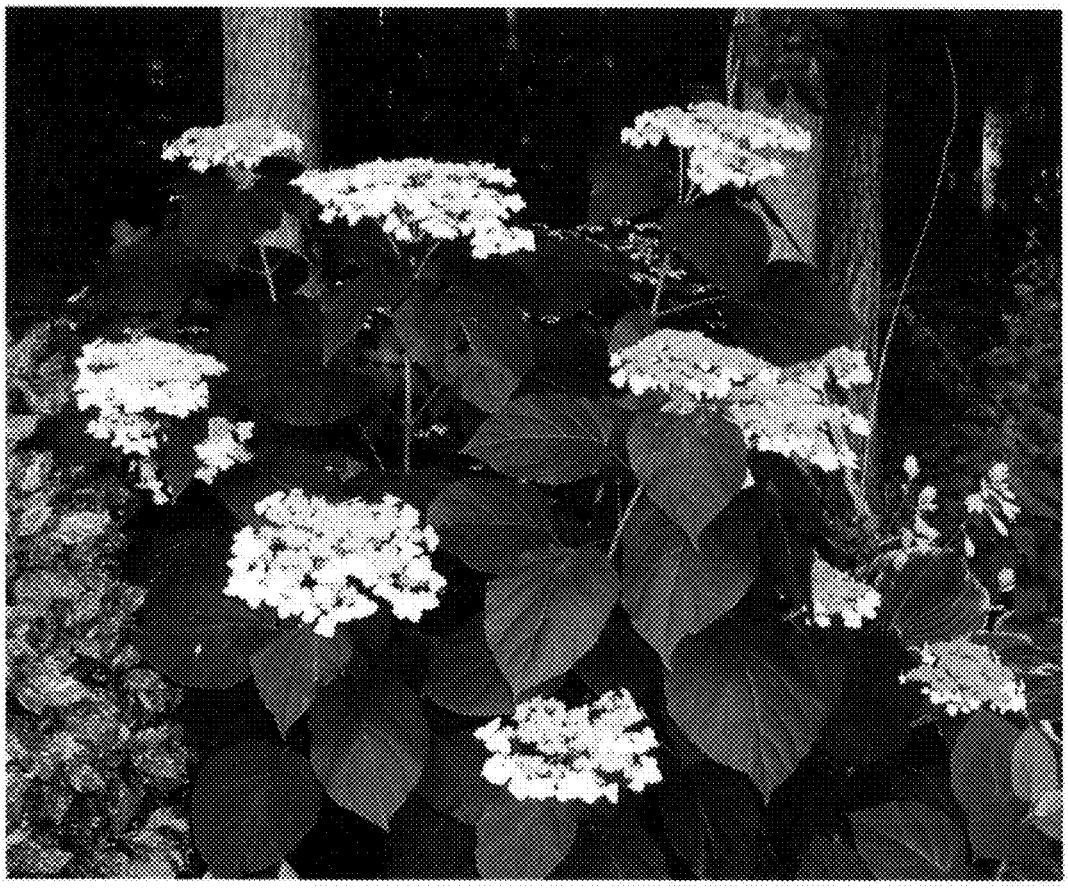
Figure 2:
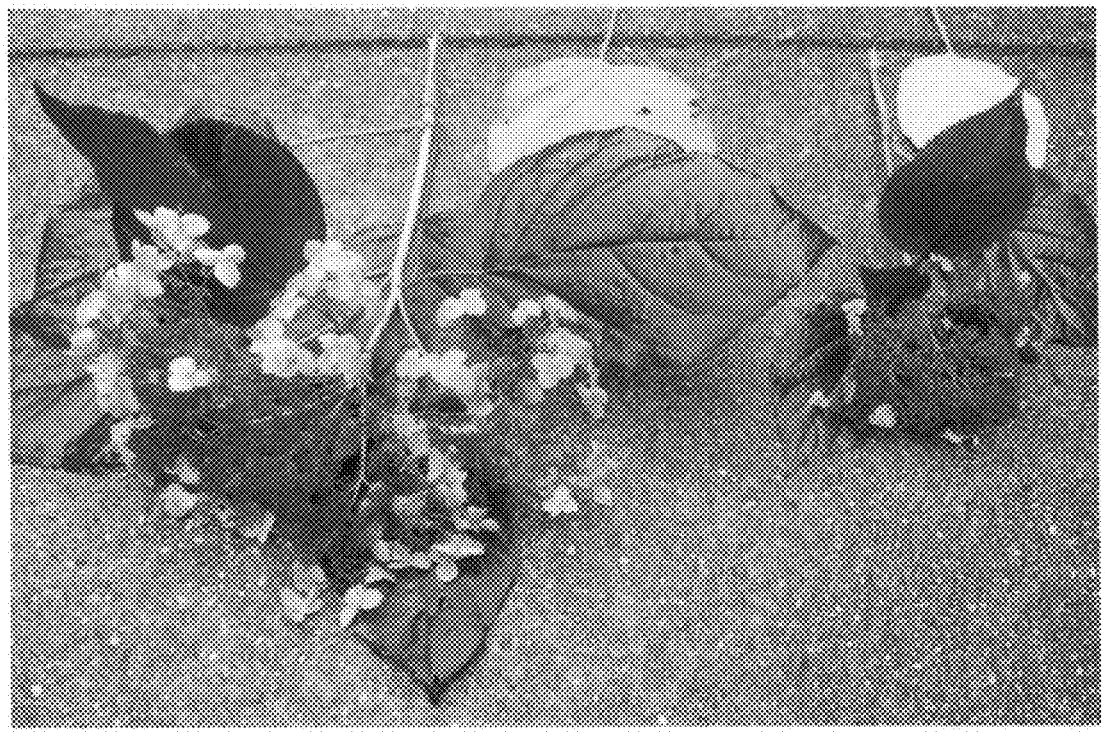

The photograph in FIG. 2 provides a view of a cut stem of 'Haas' Halo' (left) in comparison to a cut stem of 'Dardom' (right) and depicts the difference between the two cultivars in terms of inflorescence size and leave size. The colors in the photographs are as close as possible with the digital photography and printing techniques utilized and the color codes in the detailed botanical description accurately describe the new *Hydrangea.*

BOTANICAL DESCRIPTION OF THE PLANT

The following is a detailed description of two year-old plants of 'Haas' Halo' as grown outdoors in a garden in Springfield, Pa. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Attractive coloration from mid June to late August until frost in Maryland, dried blooms remain on the plant for up to 6 months after bloom.

*Plant type.*—Deciduous shrub.

*Plant habit.*—Upright.

*Height and spread*.—Reaches 1.5 m in height and 1.8 m in width in the landscape.

*Hardiness*.—At least in U.S.D.A. Zones 3 to 8.

*Diseases resistance*.—No susceptibility or disease resistance has been observed.

*Root description*.—Fibrous, dense.

*Propagation*.—Softwood stem cuttings.

*Growth rate*.—Vigorous.

Stem description:

*Stem shape*.—Round, solid.

*Stem strength*.—Moderately strong.

*Stem color*.—Mature stem; 144D with 143C stippling, new growth; 150D with 144C stippling.

*Stem size*.—Average of 90 cm in length, average of 5 mm in width.

*Stem surface*.—Glabrous.

*Internode length*.—Average of 9 cm.

*Branching*.—Freely branched, a two year-old plant will produce an average of 15 lateral branches.

Foliage description:

*Leaf shape*.—Ovate.

*Leaf division*.—Simple.

*Leaf base*.—Rounded to slightly cordate.

*Leaf apex*.—Acuminate.

*Leaf fragrance*.—None.

*Leaf venation*.—Primarily pinnate, color matches leaf coloration on upper and lower surface.

*Leaf margins*.—Moderately serrated.

*Leaf arrangement*.—Opposite.

*Leaf attachment*.—Petiolate.

*Leaf surface*.—Leathery, Glabrous and shiny on upper surface and glaucous on lower surface.

*Leaf internode length*.—An average of 9 cm.

*Leaf size*.—An average of 16 cm in length and 13 cm in width.

*Leaf quantity*.—An average of 18 per stem.

*Leaf color*.—Newly expanded leaves upper surface; 137C, newly expanded leaves lower surface; 146C, mature leaves upper surface; 136B, mature leaves lower surface; 146B, fall leaves upper surface; 13C, fall leaves lower surface; 9D.

*Petioles*.—About 7 cm in length and 3 mm in width, color 144D with markings 60A in color, glabrous surface.

Inflorescence description:

*Inflorescence type*.—Terminal lace-cap type inflorescence comprised of rotate, star-large sterile flowers and fertile flowers.

*Lastingness of inflorescence*.—Color is retained for up to 10 weeks, dried blooms retain shape for about 6 months on the plant.

*Inflorescence number*.—One per lateral or sublateral stem if pinched, about 30 on a two-year-old plant.

*Inflorescence size*.—Average of 8 cm in height and 35 cm in diameter.

*Flower number*.—An average of 50 sterile flowers per inflorescence and 475 fertile flowers per inflorescence.

*Flower fragrance*.—None.

*Flower aspect*.—Upright to outward.

*Flower size*.—Sterile flowers; an average of 3 cm in diameter and 1.5 cm in depth, fertile flowers; an average of 0.5 cm in diameter and 1 cm in depth.

*Flower buds*.—Sterile flowers; an average of 3 mm in length and 1.5 mm in width, globose in shape, 145C in color, glabrous surface, fertile flowers; average of 2 mm in length and 1 mm in width, globose in shape, 145D in color, glabrous surface.

*Peduncles*.—Strong, extension of stem, average of 2 cm in length and 2 mm in width, 150C in color, surface is pubescent.

*Pedicels*.—Sterile flowers; moderate in strength, an average of 2 mm in length and 1 mm in width, 150C in color, surface is smooth and dull, held at an average angle of 45°, fertile flowers; an average of 1 mm in length and 1 mm in length, moderate in strength, texture is smooth, dull.

*Sepals*.—Sterile flowers; 4, un-fused, slightly overlapping, rotate in arrangement, smooth, dull and glabrous on both surfaces, ovate in shape, held horizontal when fully open, entire margin, apex is broadly acute, broadly acute base, average of 3 cm in length and 1 cm in width, color upper and lower surface when newly opened in early summer; 144D, color when mature in late summer; 144D, fertile flowers; 4, un-fused, slightly overlapping, rotate in arrangement, smooth, dull and glabrous on both surfaces, ovate in shape, entire margin, apex is obtuse, base is orbicular, average of 13 mm in length and 10 mm in width, color upper and lower surface is 4D, color when immature and mature; 144D, lower surface 4D.

*Petals*.—Fertile flowers; 4, un-fused, rotate in arrangement, smooth, dull and glabrous on both surfaces, ovate in shape, entire margin, apex is acute, base is truncate, center (eye of sterile flowers); 2 mm in diameter, 145C in color, sterile flowers (eye); 1 mm in diameter and 145C in color.

Reproductive organs (fertile flowers):

*Stamens*.—Average of 10, anther is about 1 mm in length and 145D in color, filament is an average of 1 mm in length and 158B in color, pollen is minute in quantity and 158D in color.

*Pistils*.—Average of 3, average of 2.5 mm in length, 149B in color, style is an average of 2 mm in length, stigma is flattened on the of the style and 150A in color.

*Fruit and seed*.—None observed.

It is claimed:

1. A new and distinct cultivar of *Hydrangea* plant named 'Haas' Halo' substantially as herein illustrated and described.

* * * * *